United States Patent [19]

Huang

[11] Patent Number: 4,898,991

[45] Date of Patent: Feb. 6, 1990

[54] NEW PERFLUOROPOLYETHERS

[75] Inventor: Hsu-Nan Huang, Newark, Del.

[73] Assignee: E. I. Du Pont de Nemours and Company, Wilmington, Del.

[21] Appl. No.: 303,151

[22] Filed: Jan. 30, 1989

[51] Int. Cl.$^4$ ............................................. C07C 43/12
[52] U.S. Cl. .................................... 568/615; 568/677; 252/52 A; 252/54; 228/242
[58] Field of Search ................................. 568/615, 677

[56] References Cited

U.S. PATENT DOCUMENTS 3,962,348  6/1976  Benninger et al. .

FOREIGN PATENT DOCUMENTS 0148482  7/1985  European Pat. Off. .
0302392  2/1989  European Pat. Off. .
1450467  9/1976  United Kingdom .

OTHER PUBLICATIONS

A. V. Tumanova et al., Zhurnal Obshchei Khimii, vol. 35, No. 2, 339 (1965).

Primary Examiner—Howard T. Mars
Attorney, Agent, or Firm—Charles E. Krukiel

[57] ABSTRACT

New perfluoropolyethers, such as perfluoro-4,7,10-trioxa-5-methyleicosane, are useful as vapor phase soldering fluids and convection cooling liquids.

8 Claims, No Drawings

NEW PERFLUOROPOLYETHERS

BACKGROUND OF THE INVENTION

The present invention relates to novel compounds of the general class of perfluorinated compounds known as perfluoropolyethers and to their corresponding intermediates which are addition compounds of perfluorovinyl ethers and fluorinated monohydric alcohols.

Perfluoropolyethers possess excellent chemical and thermal stability which ensures a wide field of application for these compounds. They are useful as heat transfer media, sealing liquids, lubricants under extreme chemical conditions, additives for oils and greases, turbine propellents and hydraulic liquids. They exhibit low dielectric constants, high breakdown voltages and low loss factors in alternating fields, which makes them particularly suited for applications in the electrical area. In the electronics industry, for example, perfluoropolyethers are particularly useful as vapor phase soldering fluids. They also find applications as convection cooling liquids in transformers or similar devices. Their excellent dissolving power for oxygen and carbon dioxide enables them to be used as oxygen conveyers in heart-lung machines and also directly as blood substitutes in living organisms. These products also find applications in many spheres of nuclear and chemical engineering. Because of their outstanding chemical resistance they are superior to the propylene oxide fluids that hitherto dominated these application fields, especially at temperatures above 200° C.

Currently available vapor phase soldering fluids can be relatively expensive to manufacture, or they may release toxic vapors at the temperatures at which they are used. In addition, some have a high solubility in soldering rosin which requires expensive reclamation and reduces fluid life.

Compositions which most closely resemble the compositions of this invention can be found in U.S. Pat. No. 3,962,348 and its British counterpart, GB No. 1 450 467. These two patents describe polyfluoroethyl and polyfluoropropyl ethers having the following formula:

$$[C_xF_{2x+1}OCF_2]_aRf[OC_xF_{2x+1}]_b$$

where
$Rf = C_nF_{2n+2-(a+b)}$;
$n = 1-10$;
$a,b = 0-4$;
with $a+b$ greater or equal to 1; and
$x = 2$ or $3$.

Perfluoropentaerythritol tetraethyl ether and perfluoropentaerythritol tetrapropyl ether are examples of such compounds. Both patents describe the synthesis of aliphatic and cyclic perfluoroalkyl ethers in high yields in which tetrafluoroethylene or hexafluoropropylene adducts of aliphatic or cyclic alcohols are subjected to electrofluorination.

The reaction of a perfluorovinyl ether and a monohydric alcohol is described by A. V. Tumanova et al., in *Zhurnal Obshchei Khimii*, Vol. 35, No. 2,399 (1965). The addition compound formed by methanol and perfluoromethyl vinyl ether, which is described therein, differs from the intermediate products of the present invention by virtue of the fact that the alcohol used is not fluorinated. Furthermore, no subsequent fluorination step to produce a perfluoropolyether is described. No prior art is known which describes addition compounds made from the perfluorovinyl ethers and fluorinated monohydric alcohols which are used in the present invention.

SUMMARY OF THE INVENTION

This invention is the discovery and synthesis of a new class of perfluoropolyethers and their corresponding intermediates which are addition compounds of perfluorovinyl ethers and fluorinated monohydric alcohols.

These perfluoropolyethers are described by the following formula (I):

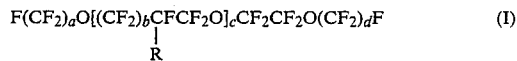

(I)

where
$a = 1-6$;
$b = 0-2$, with the proviso that when $b = 0, R = CF_3$, and when $b = 1$ or $2, R = F$;
$c = 0-8$; and
$d = 5-18$.

Examples of the novel compounds of the invention are:
$CF_3OCF_2CF_2O(CF_2)_5F$ which is perfluoro-2,5-dioxadecane;
$CF_3OCF_2CF_2CF_2OCF_2CF_2O(CF_2)_6F$ which is perfluoro-2,6,9-trioxapentadecane;

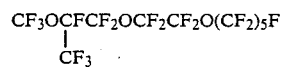

which is perfluoro-2,5,8-trioxa-3-methyltridecane;

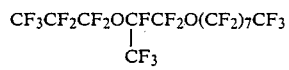

which is perfluoro-4,7-dioxa-5-methylpentadecane;

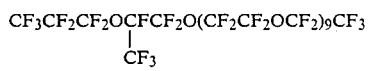

which is perfluoro-4,7,10-trioxa-5-methyleicosane;
$CF_3CF_2CF_2OCF_2CF_2O(CF_2)_7CF_3$ which is perfluoro-4,7-dioxapentadecane; and
$CF_3CF_2CF_2OCF_2CF_2O(CF_2)_9CF_3$ which is perfluoro-4,7-dioxaheptadecane.

The compounds of the invention are produced by an addition reaction between perfluorovinyl ethers and fluorinated monohydric alcohols which results in the formation of partially fluorinated intermediates which are also novel compounds within the scope of the invention. The latter are converted to perfluorinated products by a controlled photo-assisted fluorination process. A desirable feature of the preparation of the compounds of this invention is that solvents are not required in either of the process steps.

The compounds of the present invention possess excellent chemical stability. They are extremely resistant to attack by oxygen, fluorine or other very aggressive chemicals. They are stable at high temperature, e.g., over 400° C. by Differential Thermal Analysis under nitrogen. These properties make them particularly useful in the numerous applications previously described for perfluoropolyethers. The compounds of the invention are extremely effective as vapor phase soldering fluids, due to their narrow boiling point range, preferably less than 5° C. and most preferably less than 3° C. The compounds, which are useful as vapor phase soldering fluids, have their narrow boiling point range between 180° and 280° C., and preferably between 210° and 275° C. A further advantage of these compounds is that they generate very little highly toxic vapor, such as perfluoroisobutylene, during the soldering process, as which can occur with some perfluoro compounds which have been used for this purpose.

DETAILED DESCRIPTION OF THE INVENTION

The compounds of the invention are prepared by a two-step process comprising an addition reaction between perfluorovinyl ethers and fluorinated monohydric alcohols, followed by photo-assisted direct fluorination. Solvents are not required in either process step.

The perfluorovinyl ethers are selected from a group of compounds which can be represented by the formula (II):

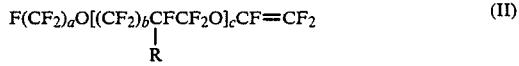

where
 a = 1–6;
 b = 0–2, with the proviso that when b = 0, R = $CF_3$, and when b = 1 or 2, R = F; and
 c = 0–8.

Examples of suitable perfluorovinyl ethers (II) are:
$CF_3OCF=CF_2$ (perfluoro-(methyl vinyl)-ether);
$CF_3CF_2OCF=CF_2$ (perfluoro-ethyl vinyl)-ether);
$CF_3CF_2CF_2OCF=CF_2$ (perfluoro-(propyl vinyl)-ether);
$CF_3CF_2OCF_2CF_2OCF=CF_2$ (perfluoro-(3-oxapentyl vinyl)-ether);
$CF_3CF_2CF_2OCF_2CF_2CF_2OCF=CF_2$ (perfluoro-(4-oxaheptyl vinyl)-ether); and

(perfluoro-(2-methyl-3-oxahexyl vinyl)-ether).

The fluorinated monohydric alcohols useful in the first step of the process are represented by the formula (III):

where
 X = H or F;
 d = 4–16; and
 e = 1–2.

Examples of suitable fluorinated monohydric alcohols (III) are:
$HCF_2CF_2CF_2CF_2CH_2OH$ (1H,1H,5H-octafluoro-1-pentanol);
$CF_3(CF_2)_3CH_2OH$ (1H,1H-nonafluoro-1-pentanol);
$CF_3(CF_2)_3CH_2CH_2OH$ (1H,1H,2H,2H-nonafluoro-1-hexanol);
$CF_3(CF_2)_7CH_2CH_2OH$ (1H,1H,2H,2H-heptadecafluoro-1-decanol); and
$CF_3(CF_2)_5CH_2CH_2OH$ (1H,1H,2H,2H-tridecafluoro-1-octanol).

To produce a partially fluorinated intermediate, the appropriate alcohol is charged to a reactor equipped with a stirrer, thermometer and a condenser maintained at −78° C. with dry ice. The alcohol is heated to 50° to 70° C. and, with stirring, a sodium hydride dispersion in mineral oil is slowly added. A dispersion containing 50 to 60% sodium hydride is usually used, and the amount of sodium hydride on the alcohol is in the range of 5 to 10 mole percent. The sodium hydride is added over a period of 5 to 60 minutes and produces a rise in temperature of a few degrees and increases the pH to about 10-11. After addition of the sodium hydride, the reaction mixture is heated, and the temperature is brought into the range of 70° to 95° C. The perfluorovinyl ether is then slowly added with continuous stirring. A convenient way to add the ether component is by means of a syringe pump with the delivery rate set to complete addition of the ether in 1 to 3 hours. The mixture is stirred for a further 1 to 2 hours while maintaining the temperature in the range of about 70° to 95° C.

It is preferred to use an excess of the alcohol component (III) and the amount of ether component (II) added is 80 to 95 mole percent based on the alcohol initially charged to the reactor. The addition reaction which gives rise to the novel intermediate compounds is illustrated by the following generalized equation (1):

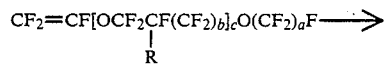

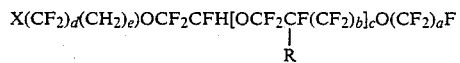

where
 a = 1–6;
 b = 0–2, with the proviso that when b = O, R = $CF_3$, and when b = 1–2, R = F;
 c = 0–8;
 d = 4–16;
 e = 1–2; and
 x = H or F.

The intermediate is recovered by vacuum distillation, and it and any unreacted components are quantitatively analyzed by Gas Chromatography. Purity of the intermediate product is in excess of 90% and yields, based on the perfluorovinyl ether charged to the reactor, are in the range of 40 to 80%, usually in excess of 70%.

The partially fluorinated polyether intermediate is then converted to a perfluoropolyether by a photo-assisted direct fluorination process analagous to that described in U.S. application Ser. No. 195,912. In the process for preparing compounds of the present invention, it is preferred that a solvent is not used, and the reaction may be subjected to an ultra-violet radiation source throughout, rather than just in the last stage of the fluorination as in the process of U.S. application Ser. No. 195,912. When solvents are not used the resulting simplification of the procedure offers significant economic benefits. If solvents are used, which is within the discretion of the operator, the requirements for the choice of suitable solvents are the same as those described in U.S. application Ser. No. 195,912.

The polyether intermediate is charged to a TEFLON FEP® reactor, similar to that described in U.S. Ser. No. 195,912. The reactor is irradiated immediately and throughout the fluorination using an ultra-violet lamp. The reactant is cooled, agitated and purged with an inert gas, such as, for example, nitrogen, to displace any oxygen from the system.

The fluorine gas is diluted with an inert gas, such as helium, neon, argon or nitrogen to an initial concentration of from 1% to about 10% by volume. For reasons of economy, the preferred inert gas diluent is nitrogen. The fluorine is introduced into the reactor at an initial concentration which can range from 5% to about 20% by volume. If the reaction conditions are made too vigorous in the initial stages of the reaction by using an excessively high concentration of fluorine, the polyether intermediate may be subjected to degradative attack, producing many undesirable by-products and consequently poor yields of perfluoropolyether. It is well known that a high concentration of fluorine in the early stages of a fluorination reaction can lead to fragmentation of chemical bonds. These undesired side reactions can be minimized by initiating the fluorination under mild conditions. For these reasons it is preferred that the initial concentration of fluorine not exceed 5 or 6% by volume.

The initial concentration of fluorine in the feed gas is gradually increased according to a predetermined timed sequence to 50% by volume over the course of 0.5 to 4 hours. The timing of the reaction sequence is determined by the amount of hydrogen present in the substrate. If the substrate has greater than about 3% hydrogen by weight, then the increase in the concentration of fluorine in the feed gas must occur over the course of about 3 hours. If the substrate contains 0.5% hydrogen by weight or less, then the concentration of fluorine can be increased more rapidly. More particularly, the predetermined timed sequence comprises typically (a) maintaining the initial fluorine concentration in the inert gas stream until from 1 to and including 5% of the theoretical amount of fluorine has been introduced into the reaction solution;

(b) increasing the fluorine concentration to a value up to and including 33% by volume and maintaining that concentration until up to and including 12% of the theoretical amount of fluorine has been introduced into the reaction solution;

(c) increasing the fluorine concentration to a value up to and including 50% by volume and maintaining that concentration until up to and including 120% of the theoretical amount of fluorine has been introduced into the reaction solution; and (d) increasing the fluorine concentration to the desired realistic maximum value and maintaining that concentration until up to and including 200% of the theoretical amount of fluorine has been added to the reaction solution.

It will be recognized that the concentration of fluorine in the feed gas can be increased by up to 41% by volume or higher in any single step of the sequence and that the sequence may consist of fewer steps as desired. However, a preferred maximum increase for each step is 20% by volume which permits a relatively gradual increase in the concentration of fluorine throughout the reaction and tends to avoid complications which can be introduced by an uncontrolled fluorination. As the concentration of fluorine in the reaction is increased, it is often desirable to reduce the flow rate of fluorine-containing feed gas into the reactor for economy and to reduce the waste load on the fluorine scrubbing system. After the concentration of fluorine in the feed gas reaches preferably about 50% by volume, the fluorine concentration is maintained constant thereafter for an additional 3 to 10 hours or until the reaction is complete. In practice, the fluorine concentration in the feed gas may be raised to 75% by volume or higher, but no improvement in yield is expected, and safety considerations may suggest that fluorine concentrations higher than 50% by volume should be avoided. The feed gas is passed continuously through the reactor during the reaction, and gas leaving the reactor is passed through sodium fluoride and alumina or carbon absorbers to remove HF and fluorine, respectively, in the effluent gas.

The course of the reaction can be monitored using gas chromatography to follow the disappearance of the intermediates and appearance of the product. The reaction is judged to be complete when there are no fluorine-replaceable hydrogens remaining in the reaction mixture as judged by proton NMR spectroscopy.

It will be appreciated by those skilled in the art that each polyether intermediate to be fluorinated will present slightly different characteristics which must first be evaluated by running several small scale reactions to define the optimum concentration, temperature, timing of fluorine concentration increases, and total reaction time for that material or substrate. The invention is further illustrated by the following examples.

EXAMPLE 1

65 g (0.14 mole) of 1H,1H,2H,2H-heptadeca-fluoro-1-decanol, $CF_3(CF_2)_7CH_2CH_2OH$, was charged into a 4-neck round bottom flask equipped with a mechanical stirrer, a thermometer and a dry ice cooled condenser. The substrate was heated to 60° C. and 0.4 g (0.01 mole) of sodium hydride (60% dispersion in mineral oil) was slowly added. The temperature rose 8° C. during the addition of the sodium hydride and the pH increased to 11. After addition of the sodium hydride the mixture was heated to 80° C. 35 g (0.13 mole) of perfluoro(propyl vinyl) ether, $CF_3CF_2CF_2OCF{=}CF_2$, was added at the rate of 0.2 ml/min by means of a syringe pump to the stirred mixture. The perfluoro(propyl vinyl) ether (bp 36° C.) was previously prepared using the procedure described in U.S. Pat. No. 3,321,532, teachings of which are incorporated herein by reference. The reaction mixture was maintained at 80° C. with stirring for 1 hour after completing the addition of the perfluoro(propyl vinyl) ether.

80 g of colorless liquid was obtained by vacuum distillation (27 mm Hg). The distillate was analyzed by Gas Chromatographic analysis, using an 8 meter×¼ inch column packed with 10% Fluorosilicon (SP-2401) on 80/100 Supelloport, and was found to consist of 91.3% of the expected fluoropolyether, $CF_3CF_2CF_2OCFHCF_2OCH_2CH_2CF_2(CF_2)_6CF_3$ (I) and 8% of unreacted 1H,1H,2H,2H-heptadecafluoro-1-decanol. Calculated yields of (I) were 79.2%, based on 1H,1H,2H,2H-heptadecafluoro-1-decanol and 75.8%, based on perfluoro(propyl vinyl) ether. The boiling point of (I) was 234° C. NMR analysis gave three $^1H$ signals: A=1.9 ppm (triplet and triplet), B=3.72 ppm (triplet) and C=5.45 ppm (doublet and triplet); with coupling constants: $J_{AB}=6.2$, $J_{DA}=17.9$, $J_{EC}=53.1$ and $J_{FC}=2.9$. The $^1H$ NMR assignments are:

$$E_{CF} \quad B \quad A \quad D \qquad (I)$$
$$CF_3CF_2CF_2OCFHCF_2OCH_2CH_2CF_2(CF_2)_6CF_3.$$

40 ml (0.096 mole) of (I) and 200 ml of Krytox ® oil (E. I. du Pont de Nemours & Co.) were charged to a Teflon FEP ® reactor and irradiated by a 450 watt medium pressure Hanovia ultra-violet lamp before introducing fluorine into the reactor. The temperature of the liquid was maintained at 20° C. by means of an internal copper cooling coil. The liquid was purged with nitrogen (200 cc/min) for 1 hour. Fluorine diluted with nitrogen was then added as follows: $F_2/N_2$ (cc/min): 10/50 for 15 min, 24/50 for 30 min, 50/50 for 4θ hours, 50/30 for 15 min, 30/30 for 2 hours and 200/0 for 45 min. The fluorinated liquid was treated with 20 g of aluminum oxide and 30 g of sodium fluoride with stirring at 80° C. for 1 hour. The solids were removed by filtration and 55 g of product was recovered by vacuum distillation, (10 mm Hg). The boiling point of the perfluoropolyether (II) was 215° C. and the yield, based on the starting fluoropolyether (I) was 69.9%. The structure $CF_3CF_2CF_2OCF_2CF_2O(CF_2)_9CF_3$ (II) was confirmed by $^{19}F$ NMR. Compound (II) was shown by Differential Thermal Analysis to be stable up to 400° C.

EXAMPLE 2

51 g (0.14 mole) of 1H,1H,2H,2H-tridecafluoro-1-octanol $CF_3(CF_2)_5CH_2CH_2OH$ was charged to the equipment described in Example 1. Four tenths of a gram (0.01 mole) of sodium hydride (as a 60% dispersion in mineral oil) was added. The temperature rose 4° C. and the pH increased to 11. The mixture was heated at 88° C. for 1 hour. Perfluoro(propyl vinyl) ether (35 g, 0.13 mole) was added as described in Example 1. Vacuum distillation at 25 mm Hg gave 68 g of a colorless liquid which had a boiling point of 207° C. This composition gave three $^1H$ NMR signals: A=1.8 ppm (triplet and triplet), B=3.2 ppm (triplet) and C=5.4 ppm (doublet and triplet); with coupling constants: $J_{AB}$=6.2, $J_{FC}$=2.9, $J_{DC}$=53.3 and $J_{EA}$=17.9. The $^1H$ NMR assignments are:

$$DC \quad F \quad B \quad A \quad E \qquad (III)$$
$$CF_3CF_2CF_2OCFHCF_2OCH_2CH_2CF_2(CF_2)_4CF_3.$$

Gas Chromatographic analysis showed the liquid comprised 95.8% of the expected fluoropolyether. There was 2.73% of unreacted 1H,1H,2H,2H-tridecafluoro-1octanol. Yields of (III) were 76.5% based on 1H,1H,2H,2H-tridecafluoro-1-octanol and 78% based on perfluoro(propyl vinyl) ether.

50 ml (0.12 mole) of (III) and 200 ml of Krytox ® oil were charged to the fluorination reactor as described in Example 1. After purging the liquid with nitrogen for 1 hour, fluorine diluted with nitrogen was added as follows: $F_2/N_2$ (cc/min): 10/50 for 15 min, 24/50 for 30 min, 50/50 for 5.5 hours, 0/200 for 1 hour. The temperature was maintained at 19° C. throughout the fluorination. The fluorinated products were treated with 20 g of alumina and 30 g of sodium fluoride at 80° C. for 1 hour. After removing solids by filtration 60 g of a colorless liquid product was obtained by vacuum distillation at 25 mm Hg. The structure of the product $CF_3CF_2CF_2OCF_2CF_2O(CF_2)_7CF_3$ (IV) was confirmed by $^{19}F$ NMR. The boiling point of (IV) was 185° C. and the yield, based on the fluoropolyether (III), was 69.4%. Compound (IV) was shown by Differential Thermal Analysis to be stable up to 400 ® C.

EXAMPLE 3

50 g (0.11 mole) of 1H,1H,2H,2H-heptadecafluoro-1-decanol was reacted with 0.3 g (0.008 mole) of sodium hydride and the 38 g (0.09 mole) of perfluoro-(2-ethyl-3-oxahexyl vinyl) ether by the procedures described in Example 1. 6 g of unreacted perfluoro-(2-methyl-3-oxyhexyl vinyl) ether was removed by simple distillation. Vacuum distillation at 20 mm Hg gave 63 g of a colorless liquid. Gas Chromatographic analysis of this fraction showed it to consist of 8.4% of unreacted perfluoro-(2-methyl-3-oxahexyl vinyl) ether, 55.5% of unreacted 1H,1H,2H,2H-heptadecafluoro-1decanol and 36.1% of the desired fluoropolyether, (V). Calculated yields of (V) were 78.3% based on 1H,1H,2H,2H-heptadecafluoro-1-decanol and 41.1% based on perfluoro-(2-methyl-3-oxahexyl vinyl) ether. The boiling point of (V) was 260° C. The fluoropolyether gave three signals on $^1H$ NMR: A=1.97 ppm (triplet), B=3.79 ppm (triplet) and C=5.5 ppm (doublet); with coupling constants: $J_{AB}$=6.3, $J_{EA}$=17.6 and $J_{DC}$=53.4. The $^1H$ NMR assignments are:

$$DC \quad B \quad A \quad E \qquad (V)$$
$$CF_3CF_2CF_2OCF(CF_3)CF_2OCFHCF_2OCH_2CH_2CF_2(CF_2)_6CF_3.$$

100 ml (0.19 mole) of (V) was fluorinated using the equipment and procedure described in Example 1. After purging the starting liquid with nitrogen, (200 cc/min), fluorine diluted with nitrogen was added as follows: $F_2/N_2$ (cc/min): 3/50 for 10 min, 6/50 for 10 min, 12/50 for 10 min, 24/50 for 10 min, 50/50 for 9½ hours, 0/200 for 1 hour. The temperature was maintained at 22° C. throughout the fluorination. The fluorinated products were separated by vacuum distillation at 10 mm Hg. A colorless liquid product (168.9 g) was collected and analyzed by FTIR and GC/Mass Spec. and shown to be perfluorinated material. Structure $CF_3CF_2CF_2OCF(CF_3)CF_2OCF_2CF_2O(CF_2)_9CF_3$ (VI) was confirmed by $^{19}F$ NMR. The boiling point of (VI) was 246° C. and the yield, based on the fluoropolyether (V) was 90.0%. Compound (VI) was shown by Differential Thermal analysis to be stable up to 400° C.

EXAMPLE 4

40 g (0.11 mole) of 1H,1H,2H,2H-tridecafluoro-1-octanol was reacted with 0.3 g (0.008 mole) of sodium hydride and 38 g (0.09 mole) of perfluoro-(2-methyl-3-oxahexyl vinyl) ether using the equipment and procedure of Example 1. Vacuum distillation at 20 mm Hg yielded 55 g of a colorless liquid, which was found by Gas Chromatographic analysis to contain 23.1% of unreacted 1H,1H,2H,2H-tridecafluoro-1-octanol and 74.0% of the expected fluoropolyether, $CF_3CF_2CF_2OCF(CF_3)CF_2OCFHCF_2OCH_2CH_2CF_2(CF_2)_4CF_3$ (VII). Calculated yields of this fluoropolyether were 68% based on 1H,1H,2H,2H-tridecafluoro-1-octanol and 56.7% based on perfluoro-(2-methyl-3-oxahexyl vinyl) ether. This fluoropolyether had a boiling point of 227° C., and gave three signals on $^1H$ NMR: A=1.95 ppm (triplet), B=3.78 ppm (triplet) and C=5.5 ppm (doublet); with coupling constants: $J_{AB}$ 6.3, $J_{DC}$=53.4 and $J_{EA}$=17.4. The $^1H$ NMR assignments are:

DC B A E (VII)
CF$_3$CF$_2$CF$_2$OCF(CF$_3$)CF$_2$OCFHCF$_2$OCH$_2$CH$_2$CF$_2$(CF$_2$)$_4$CF$_3$.

110 ml (0.24 mole) of (VII) was fluorinated using the equipment and procedure described in Example 1. After purging the starting liquid with nitrogen (200 cc/min), fluorine diluted with nitrogen was added as follows: F$_2$/N$_2$ (cc/min): 3/50 for 10 min, 6/50 for 10 min, 12/50 for 15 min, 24/50 for 2½ hours, 56/50 for 8¾ hours and 0/200 for 1 hour. The fluorinated products were separated by vacuum distillation. 160.5 g of colorless liquid was collected using a vacuum of 10 mm Hg. This liquid was shown to be a perfluorinated material by FTIR and GC/Mass Spec., with the highest mass peak at m/e=419. The structure was confirmed by $^{19}$F NMR to be CF$_3$CF$_2$CF$_2$OCF(CF$_3$)CF$_2$OCF$_2$CF$_2$O(CF$_2$)$_7$CF$_3$ (VIII). The boiling point of this product was 219° C. and the yield based on the starting fluoropolyether (VII) was 85.2%. Compound (VIII) was shown by Differential Thermal analysis to be stable up to 400° C.

I claim:

1. Perfluoropolyether compounds of the formula:

$$F(CF_2)_aO[(CF_2)_b\underset{R}{C}FCF_2O]_cCF_2CF_2O(CF_2)_dF$$

where:
a=1–6;
b=0–2, with the proviso that when b=0, R=CF$_3$, and when b=1 or 2, R=F;
c=0–8; and
d=5–18.

2. The compound of claim 1 which is perfluoro-2,5-dioxadecane of the formula:

CF$_3$OCF$_2$CF$_2$O(CF$_2$)$_5$F.

3. The compound of claim 1 which is perfluoro-2,6,9-trioxapentadecane of the formula:

CF$_3$OCF$_2$CF$_2$CF$_2$OCF$_2$CF$_2$O(CF$_2$)$_6$F.

4. The compound of claim 1 which is perfluoro-2,5,8-trioxa-3-methyl-tridecane of the formula:

$$CF_3O\underset{CF_3}{C}FCF_2OCF_2CF_2O(CF_2)_5F$$

5. The compound of claim 1 which is perfluoro-4,7-dioxa-5-methyl-pentadecane of the formula:

$$CF_3CF_2CF_2O\underset{CF_3}{C}FCF_2O(CF_2)_7CF_3$$

6. A compound of claim 1 which is perfluoro-4,7,10-trioxa-5-methyleicosane of the formula:

$$CF_3CF_2CF_2O\underset{CF_3}{C}FCF_2OCF_2CF_2O(CF_2)_9CF_3$$

7. A compound of claim 1 which is perfluoro-4,7-dioxapentadecane of the formula:

CF$_3$CF$_2$CF$_2$OCF$_2$CF$_2$O(CF$_2$)$_7$CF$_3$.

8. A compound of claim 1 which is perfluoro-4,7-dioxaheptadecane of the formula:

CF$_3$CF$_2$CF$_2$OCF$_2$CF$_2$O(CF$_2$)$_9$CF$_3$.

* * * * *